United States Patent [19]

Tognazzini

[11] Patent Number: 5,771,484
[45] Date of Patent: Jun. 23, 1998

[54] AUTOMATED POSITIVE CONTROL TRAFFIC SYSTEM FOR WEATHER

[75] Inventor: Bruce Tognazzini, Woodside, Calif.

[73] Assignee: Sun Microsystems, Inc., Palo Alto, Calif.

[21] Appl. No.: 608,590

[22] Filed: Feb. 28, 1996

[51] Int. Cl.[6] .............................. G08G 1/09; G01W 1/00
[52] U.S. Cl. .......................... 701/117; 364/420; 340/601
[58] Field of Search ................................. 364/436, 437, 364/438, 420; 340/910, 601, 602; 701/117, 118, 119

[56] References Cited

U.S. PATENT DOCUMENTS

| | | | |
|---|---|---|---|
| 3,626,413 | 12/1971 | Zachmann | 343/8 |
| 4,636,643 | 1/1987 | Nakamura et al. | 250/338 |
| 4,706,086 | 11/1987 | Panizza | 340/902 |
| 4,792,803 | 12/1988 | Madnick et al. | 340/905 |
| 5,164,904 | 11/1992 | Sumner | 364/436 |
| 5,303,401 | 4/1994 | Duckeck et al. | 455/186.1 |
| 5,345,243 | 9/1994 | Levis | 342/173 |
| 5,646,853 | 7/1997 | Takahashi et al. | 364/436 |
| 5,663,710 | 9/1997 | Fasig et al. | 340/601 |
| 5,663,720 | 9/1997 | Weissman | 340/934 |

*Primary Examiner*—Michael Zanelli
*Attorney, Agent, or Firm*—McDermott, Will & Emery

[57] ABSTRACT

Systems and methods for traffic control use scanning transmissometers to determine visibility along an extended stretch of roadway. When areas of decreased visibility are detected, such as dense localized pockets of fog, appropriate warning information is provided to drivers over warning devices positioned along the roadway. Information from the transmissometers is used to develop a speed profile, that is an indication of safe speed as a function of position along the roadway. Traffic sensors detect variations in behavior from that specified by the warning devices, such as a very slow vehicle, and modifies the warning information according. A computer readable medium contains a computer program for implementing the systems and methods.

30 Claims, 17 Drawing Sheets

| MPH | FT/SEC | REACTION DISTANCE (.5 SEC) | DEACCELERATION DISTANCE | TOTAL STOPPING DISTANCE |
|---|---|---|---|---|
| 5 | 7.33 | 3.6 | 2.7 | 6.3 |
| 10 | 14.66 | 7.3 | 10.7 | 18.0 |
| 20 | 29.33 | 14.6 | 43.0 | 57.6 |
| 30 | 44.00 | 22.0 | 96.8 | 118.8 |
| 40 | 58.66 | 29.3 | 172.0 | 201.3 |
| 50 | 73.33 | 36.6 | 268.9 | 305.5 |
| 60 | 88.00 | 44.0 | 387.2 | 431.2 |
| 70 | 102.66 | 51.3 | 576.9 | 628.3 |
| 80 | 117.33 | 58.6 | 688.3 | 746.9 |

Figure 12

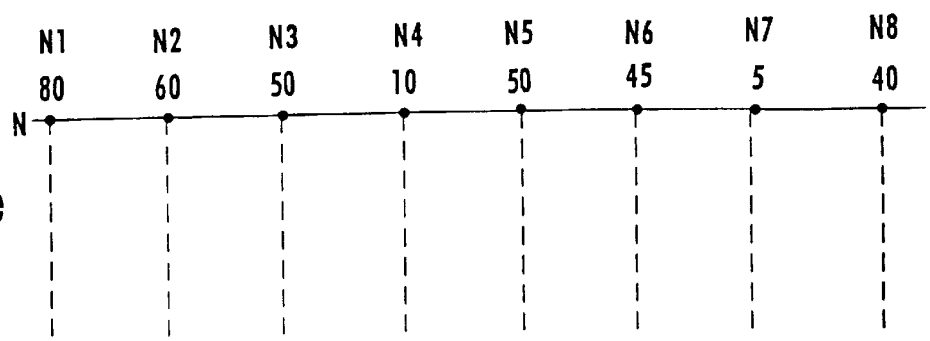
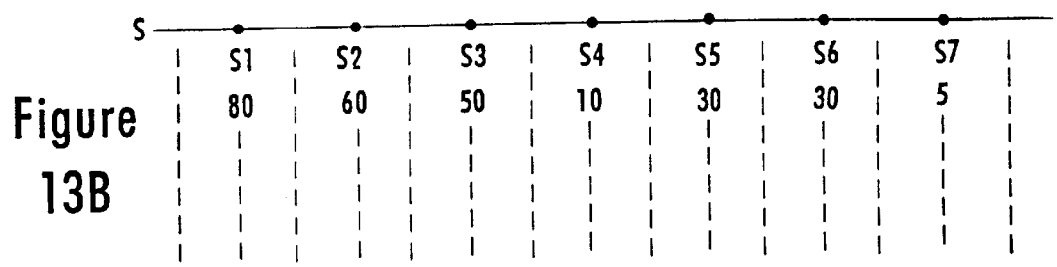
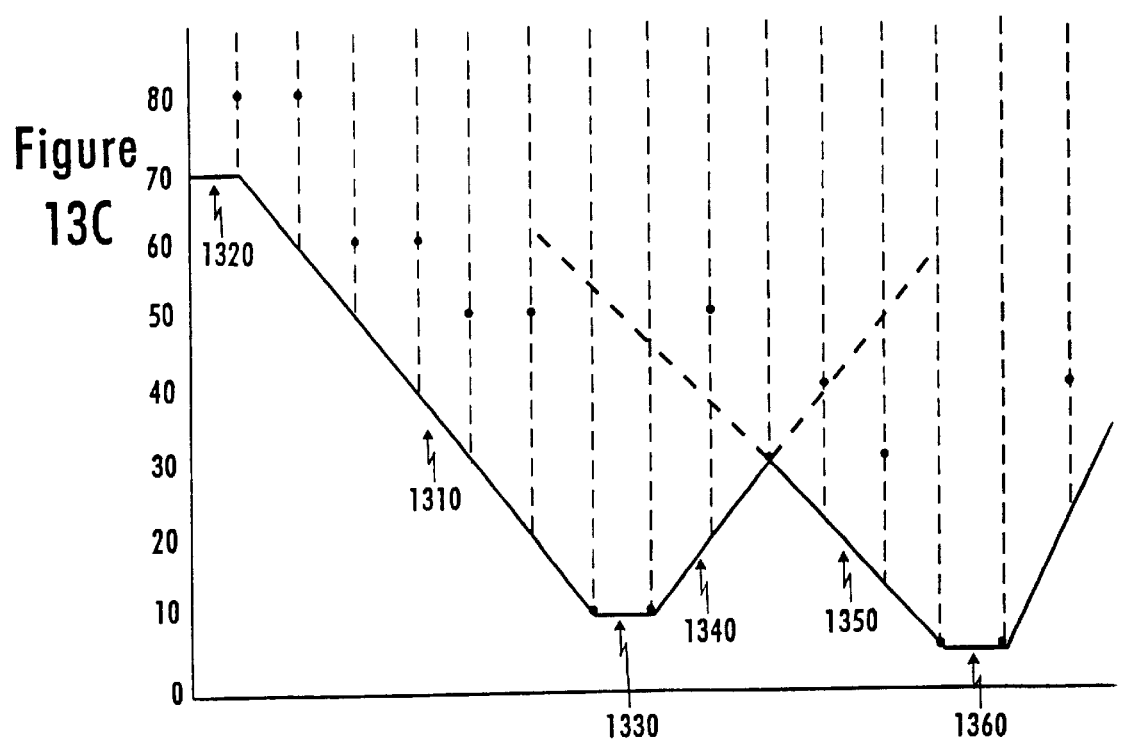

| MEASUREMENT POINT | TRANSMISSIVITY | VISIBILITY |
|---|---|---|
| 1 | 100% | >600 FT |
|   | 80%  | 431 FT |
|   | 60%  | 305 FT |
|   | 40%  | 208 FT |
|   | 20%  | 110 FT |
|   | 10%  | 40 FT |
|   | 5%   | 18 FT |
|   | 1%   | 6 FT |
| 2 | 100% | >600 FT |
|   | 80%  | 475 FT |
|   | 60%  | 320 FT |
|   | 40%  | 240 FT |
|   | 20%  | 130 FT |
|   | 10%  | 45 FT |
|   | 5%   | 22 FT |
|   | 1%   | 6 FT |
| 3 ⋮ | | |

Figure 15

AUTOMATED POSITIVE CONTROL TRAFFIC SYSTEM FOR WEATHER

BACKGROUND OF THE INVENTION

1. Field of the Invention

This invention generally relates to traffic control systems and more particularly to computer controlled traffic control systems for controlling traffic under adverse weather conditions to avoid accidents.

2. Description of Related Art

Automated traffic control systems are known in which traffic on a highway is monitored and drivers desiring to enter a highway from on-ramps are metered to limit the number entering the highway to a number consistent with the density of traffic detected. Typically, these systems utilize a red/green stop light, perhaps one for each lane of traffic entering the highway, and a sign indicating that metering is active.

Traffic monitors are also known in which wire loops are embedded in the surface of the highway to detect the presence of vehicles either through changes in magnetic response of the loop as a vehicle passes over or by detecting voltages induced in the loop by an engine ignition system.

Pneumatic systems are also known for counting traffic as a function of time of day in which an elastic tube containing a gas is deployed across at least a portion of a highway. The tube is compressed when a vehicle runs over the tube. Changes in pressure thus induced are detected and utilized to derive a count of traffic.

Computer controlled warning signs are also known in which messages about traffic conditions ahead can be displayed to motorists.

Devices for detecting the presence of particulate matter such as that emitted from smokestacks or for detecting reduced visibility due to weather conditions are known. Such devices are known as transmissometers and typically include a light source, such as a laser, and a detector for detecting either light from the light source directly or light from the light source reflected back to the detector from a reflector such as a mirror. Transmissometers operate by detecting a reduction in the intensity of light which results from the introduction of particulate matter such as smoke or intervening weather conditions such as fog.

The Problem

The class of problems solved by this invention has its genesis in a large number of multi-vehicle automobile accidents that occur in areas, such as the central valley of California, where small but very dense pockets of fog are encountered suddenly and without warning by vehicles travelling in an otherwise clear area. Because these pockets are so localized they are difficult to detect. Even if detected, warnings provided to drivers tend to lack credibility because of the frequency of false alarms generated by false detection. Further, providing warnings too much in advance of the actual fog creates a credibility problem in that drivers, seeing no apparent impediment to their visibility, disbelieve the warnings and fail to make requisite adjustments.

Another problem occurs in that each vehicle within a fog bank makes it own determination as to what a safe speed is. The only really safe speed is one in which vehicle speed is less than or equal to the speed of the vehicles in front and greater than or equal to the speed of the vehicles following.

Another problem resulting from varying fog conditions is the convoy effect. When driving in a convoy, unless speed changes are effectuated gradually, and unless each vehicle makes a concerted effort to maintain a speed very close to the vehicle in front, a condition exists in which some vehicles get widely separated. A lagging vehicle must then speed up to catch up only to find that the vehicle in front has slowed down considerably and the vehicle attempting to catch up must jam on its brakes. Vehicles following such a vehicle then must jam on their brakes and so there is an erratic flow of traffic alternating between speed up and slow down often at precipitous rates.

Another problem associated with traffic control is that individual vehicles, for whatever reason, may disregard information about safe speeds and drive either aberrationally slow or aberrationally fast.

SUMMARY OF THE INVENTION

Embodiment of the present invention overcome the problems of the prior art by providing methods, apparatus and computer program products which provide traffic warning at appropriate times to vehicles within or entering an area containing reduced visibility. The invention detects and adapts to vehicles which fail to comply with the warning information provided. The integration of environmental condition detection, traffic sensing and warning devices with a computer system permits one to achieve enhanced accident prevention under conditions of extremely localized fog or other impaired visibility in a way which goes beyond the functionality achieved by the prior art.

A traffic control system is disclosed which includes environmental condition detectors, traffic sensors, warning devices and a computer receiving information from the detectors and traffic sensors. The computer is configured to control warning devices in a way to prevent accidents or minimize damage therefrom. Typically, the environmental condition detector is a fog detector. One or more traffic sensors detect traffic speed and/or separation. The warning devices may be warning signs, signal lights, or radio broadcast devices. The computer is configured to select information for the warning devices based on information from the environmental condition detectors and from a speed profile derived for the conditions detected on the highway.

A system and method for traffic control is disclosed which uses environmental condition detectors and traffic sensors to determine road conditions and then determines the appropriate traffic information to provide to drivers over warning devices positioned along the road. Information from the detectors and sensors is used to develop a speed profile, that is, an indication of safe speed as a function of position along the road.

Also disclosed is a computer readable medium containing a process in computer program form for controlling one or more warning devices based on inputs received from environmental condition detectors and from traffic sensors positioned along a road. The process includes detecting environmental conditions in an area near the warning device and at points further along the road in the direction of travel, controlling the warning device to communicate a safe speed to drivers based on a speed profile derived from environmental conditions at one or more points along the road. A speed profile can be modified based on actual traffic conditions as detected by the traffic sensors.

Also disclosed is a safety enhanced road including a section of road with environmental condition detectors, traffic sensors and warning devices positioned along the road, each being linked to a computer which determines information to be sent over warning devices based on data from said detectors and sensors. The environmental condition detectors may include scanning transmissometers.

A method for traffic control is also disclosed in which control is provided by determining visibility at a plurality of points along a road, establishing a predetermined safe speed for each point based on the visibility at that point, determining a speed profile specifying a safe speed for nearby points based on conditions at a point, and controlling a warning system to impose a speed limit on a segment of road to the lowest of the speed profile speeds required by nearby points and the predetermined safe speed. The profile can be modified based on traffic conditions.

Also disclosed is a computer readable medium containing a process for controlling traffic based on visibility at points along a road in computer program form. The process includes establishing a predetermined safe speed for each point based on the visibility at that point, determining a speed profile specifying a safe speed for nearby points based on conditions at a point, and controlling a warning system to impose a speed limit on a segment of road equal to the lower of (1) the lowest of the speed profile speeds required by nearby points and (2) the predetermined safe speed.

Still other objects and advantages of the present invention will become readily apparent to those skilled in the art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

DESCRIPTION OF DRAWINGS

The objects, features and advantages of the invention will be apparent from the following description in which:

FIG. 12 illustrates sample stopping distance data used to infer safe speed.

FIG. 13A–13C illustrates how to calculate a safe speed in a way which minimizes convoy effect.

FIG. 15 illustrates a look up table linking transmissivity with visibility for particular measurement points.

NOTATIONS AND NOMENCLATURE

The detailed descriptions which follow may be presented in terms of program procedures executed on a computer or network of computers. These procedural descriptions and representations are the means used by those skilled in the art to most effectively convey the substance of t heir work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

The present invention also relates to apparatus for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

DESCRIPTION OF THE PREFERRED EMBODIMENT

Figure 1:
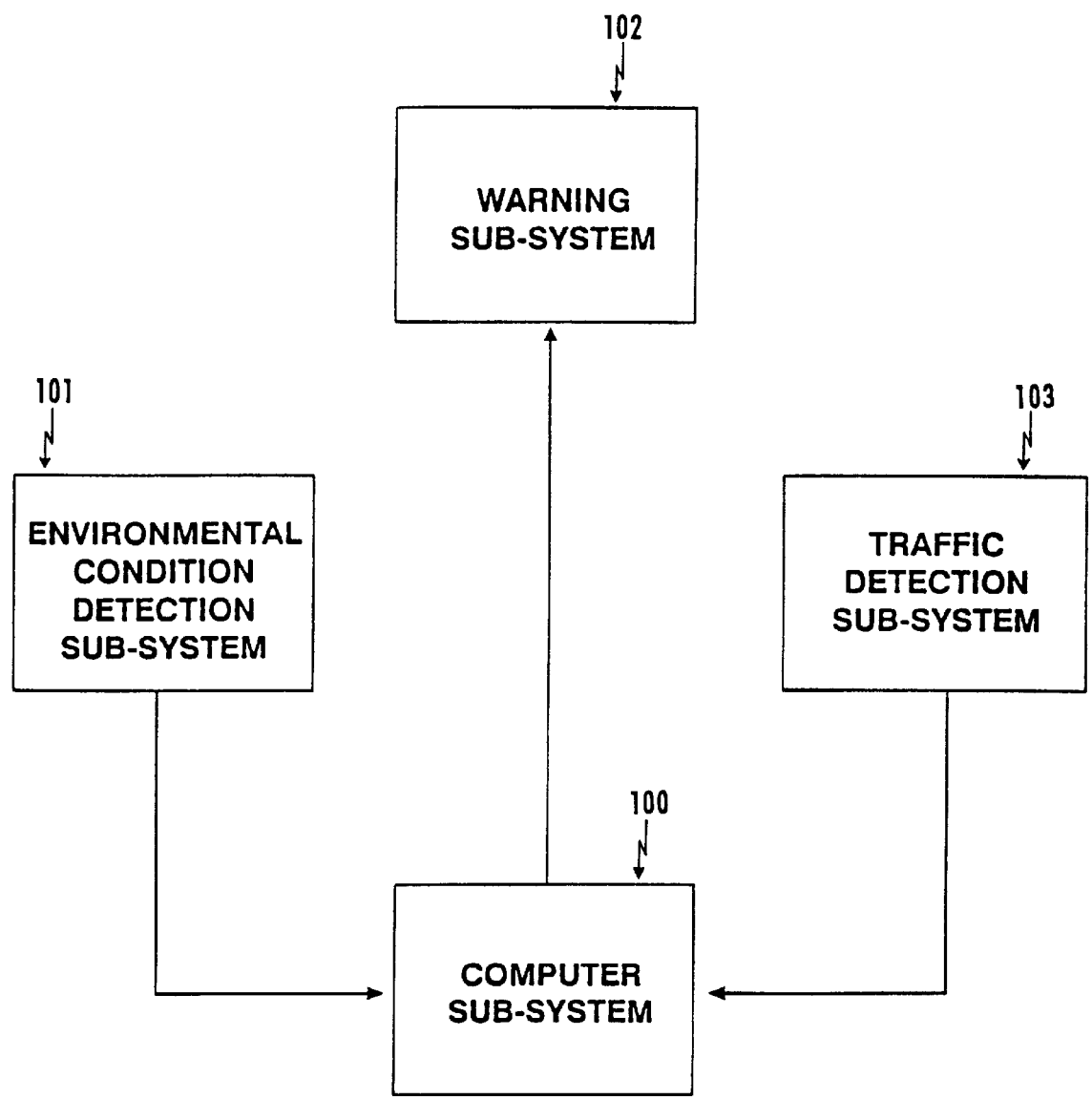
FIG. 1 illustrates a high level block diagram of a traffic control system in accordance with the invention.

FIG. 1 illustrates a high level block diagram of a traffic control system in accordance with the invention. Computer system 100 receives inputs from environmental detection sub-system 101, such as a fog detection system located along a highway being monitored, and from traffic detectors/ sensors also situated along the highway forming part of the traffic detection subsystem 103. Computer sub-system 100 utilizes the input data to determine safe speeds at various positions along the highway and to provide information to drivers about safe driving conditions using warning subsystem 102.

Environmental condition detection system 101 preferably consists of a system of fog detectors, such as transmissometers, which provide information to the computer system 100. Traffic detectors or sensors are preferably traffic radar units or alternative forms of traffic detection discussed hereinafter. Warning system 102 preferably has a plurality of illuminated signs positioned along the highway for providing information to drivers. Alternatively, warning system 102 could utilize short range AM or FM radio transmission or addressable radio links to individual vehicles for sending warning information. At one extreme, the warning sub-system could actually seize control of a vehicle and regulate its speed in an automated fashion.

Figure 2A:
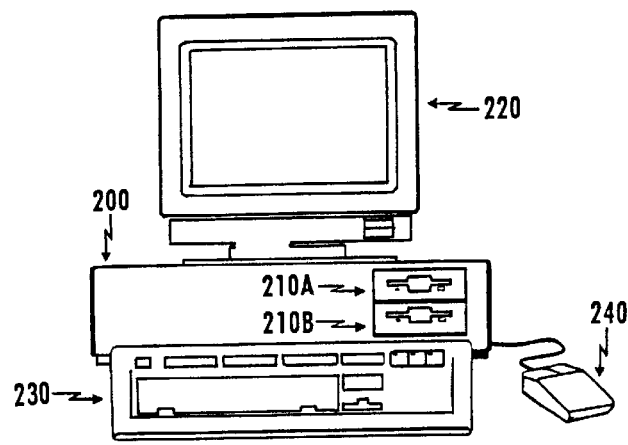
FIG. 2A illustrates a computer of a type suitable for carrying out the invention.

FIG. 2A illustrates a computer of a type suitable for carrying out the invention. Viewed externally in FIG. 2A, a computer system has a central processing unit 200 having disk drives 210A and 210B. Disk drive indications 210A and 210B are merely symbolic of a number of disk drives which might be accommodated by the computer system. Typically, these would include a floppy disk drive such as 210A, a hard disk drive (not shown externally) and a CD ROM or DVD drive indicated by slot 210B. The number and types of drives vary, typically, with different computer configurations. The computer has a display 220 upon which information is displayed. A keyboard 230 and a mouse 240 are typically available as input devices. Preferably, the computer illustrated in FIG. 2A is a SPARC workstation from Sun Microsystems, Inc.

Figure 2B:
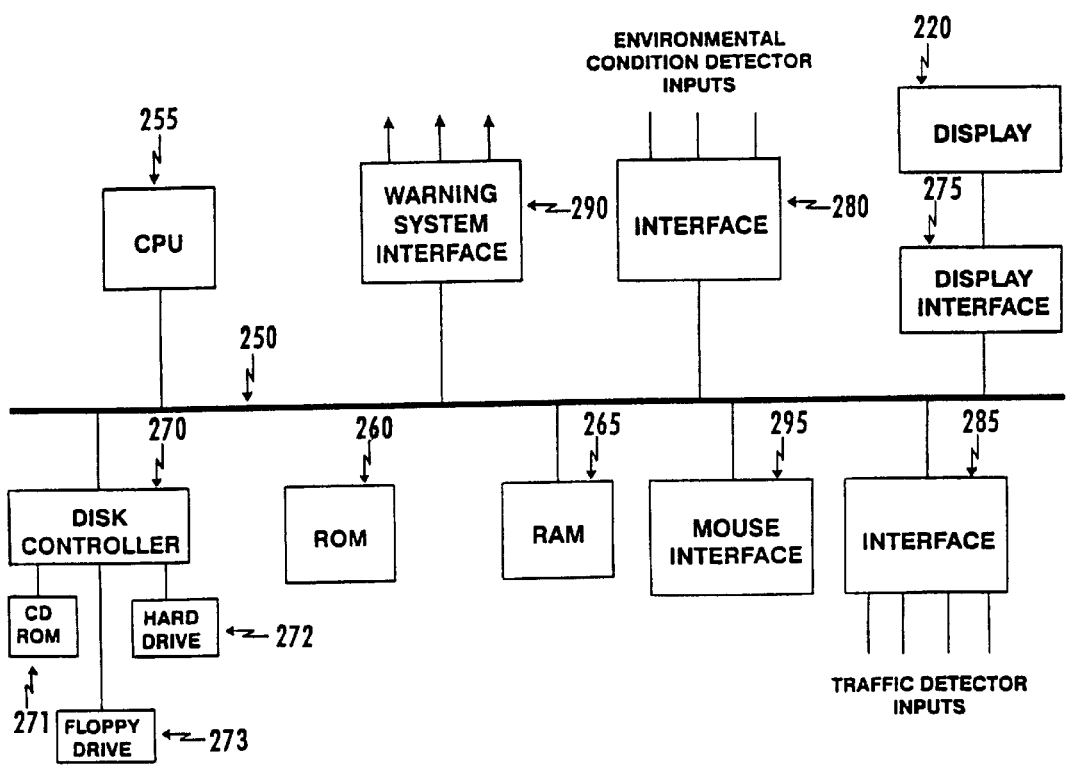
FIG. 2B illustrates a block diagram of the exemplary hardware of the computer of FIG. 2A.

FIG. 2B illustrates a block diagram of the hardware configuration of the computer of FIG. 2A. A bus 250 serves as the main information highway interconnecting the other components of the computer. CPU 255 is the central processing unit of the system, performing calculations and logic operations required to execute a program. Read only memory (260) and random access memory (265) constitute the main memory of the computer. Disk controller 270 interfaces one or more disk drives to the system bus 250. These disk drives may be floppy disk drives, such as 273, internal or external hard drives, such as 272 or CD ROM or DVD (Digital Video Disks) drives such as 271. A display interface 275 interfaces display 220 and permits information from the bus to be displayed on the display. Information from environmental condition detectors is received over interface 280 and made available over the system bus to the CPU for processing. Similarly, traffic detector information is received over interface 285 and made available for processing.

Information is sent to the elements of the warning subsystem over interface 290. Each of the interfaces 280, 285 and 290 could be combined into a single general response I/O interface servicing all of the inputs. Although individual lines are shown going to the interfaces from individual detectors and going to individual warning devices from an interface, these will typically be multiplexed and sent over a single channel, preferably a radio channel to all devices. In response to its program and to information stored in memory and to information received over the various interfaces, the computer determines the type and content of warnings to be provided over warning system 102, referred to above.

Figure 2C:
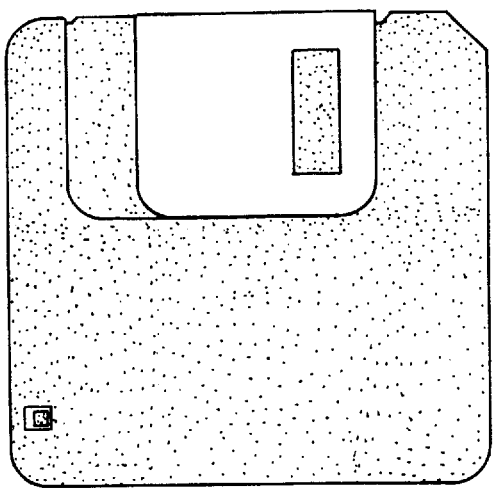
FIG. 2C illustrates an exemplary memory medium containing a program usable with the computer of FIG. 2A.

FIG. 2C illustrates an exemplary memory medium which can be used with drives such as 273 in FIG. 2B or 210A in FIG. 2A. Typically, memory media such as a floppy disk, CD ROM, or a Digital Video Disk will contain the program information for controlling the computer to enable the computer to perform its traffic control functions in accordance with the invention.

Figure 3:
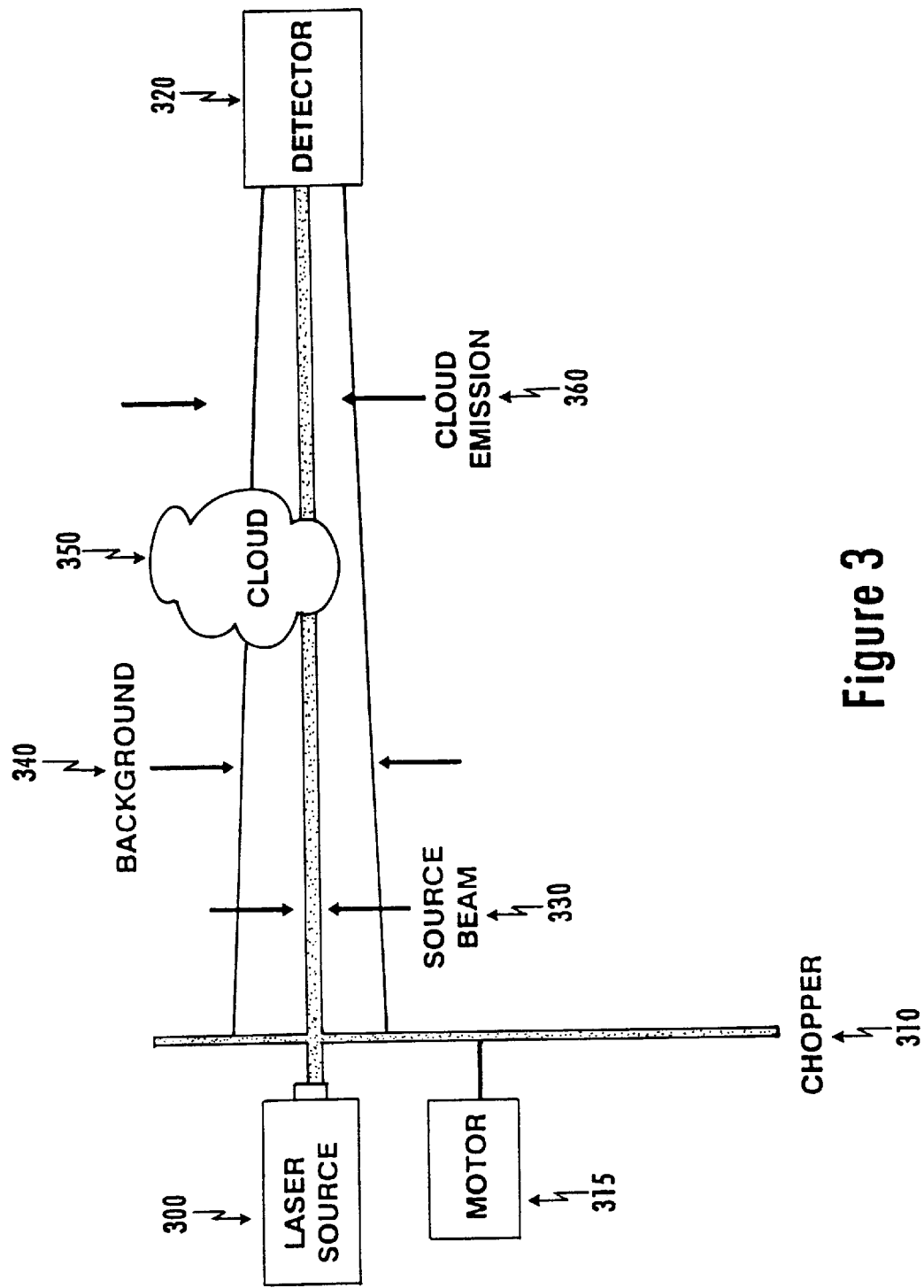
FIG. 3 illustrates a transmissometer useful for detecting fog.

FIG. 3 illustrates a transmissometer useful for detecting fog. The transmissometer shown in FIG. 3 includes a laser source 300 which emits a source beam 330 which is relatively columnated. Optionally, a chopper 310, driven by motor 315 is utilized to impose a modulation on source beam 330 to render the desired signal easily recognizable at the detector. Detector 320 contains a detecting element sensitive to the radiation from laser source 300. The aperture of the detector 320 illustrated by background range 340 includes more area than that occupied by the signal from laser source 300. Thus, in addition to the desired signal from laser source 300, detector 320 also detects background radiation from outside the source beam width. When a cloud or fog 350 interposes itself between the source and the detector, light is scattered away from the path between the laser source and the detector, thus reducing the intensity of radiation from laser source 300 received at detector 320. Because of the scattering, cloud emission 300 scatters light into the aperture of the detector 320 where it is also detected along with light from laser source 300 which is not scattered. The denser the cloud 350, the less light will be received at detector 320.

Figure 4:
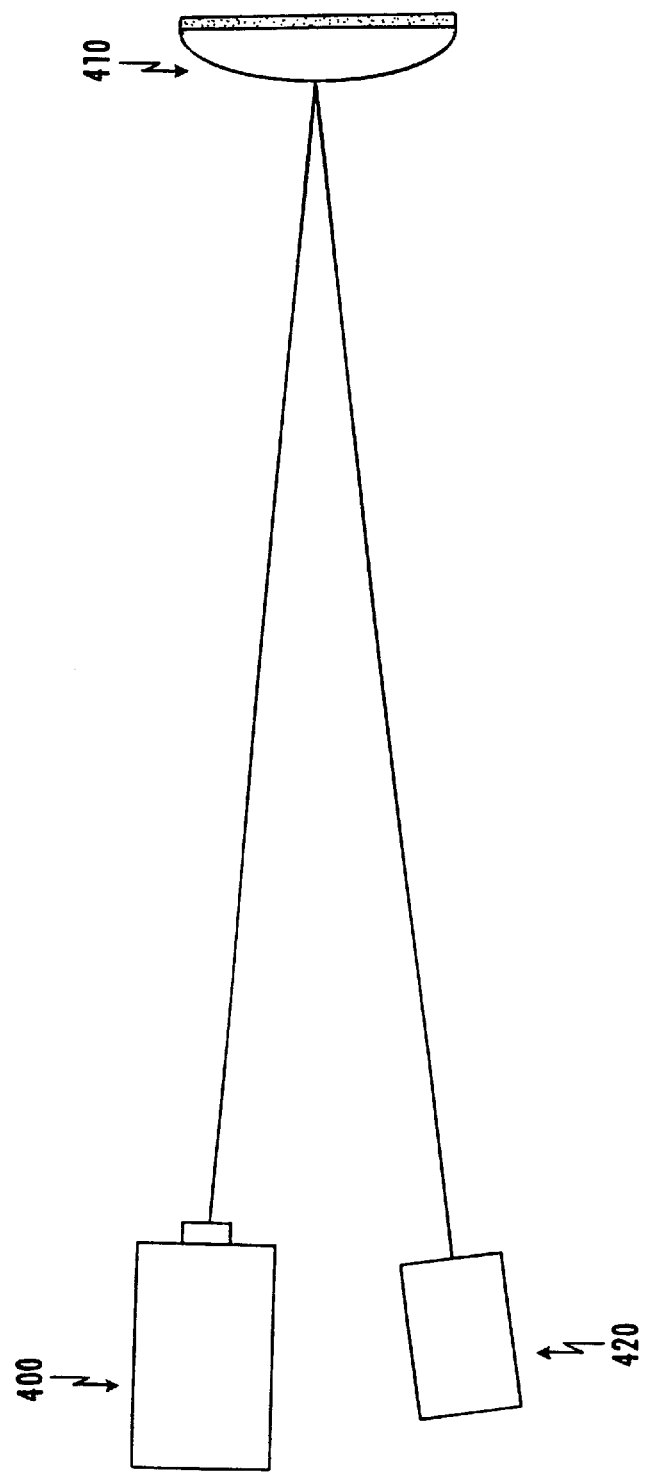
FIG. 4 illustrates a transmissometer in which the light source and the detector are located opposite of a mirror to reflect the light beam.

FIG. 4 illustrates a transmissometer in which the light source and the detector are located opposite a mirror utilized to reflect the light beam from the source to the detector. Although not illustrated in FIG. 4, detector 420 has an aperture which includes background information or noise and laser source 400 has a source beam of finite width. The optional chopper 310 is not illustrated in the FIG. 4 embodiment. The mirror 410 is slightly convex and, as shown hereinafter will result in a slight spread of the source beam which will increase the probability that signal from the source beam, when reflected from the mirror will enter the aperture of detector 420.

Figure 5A:
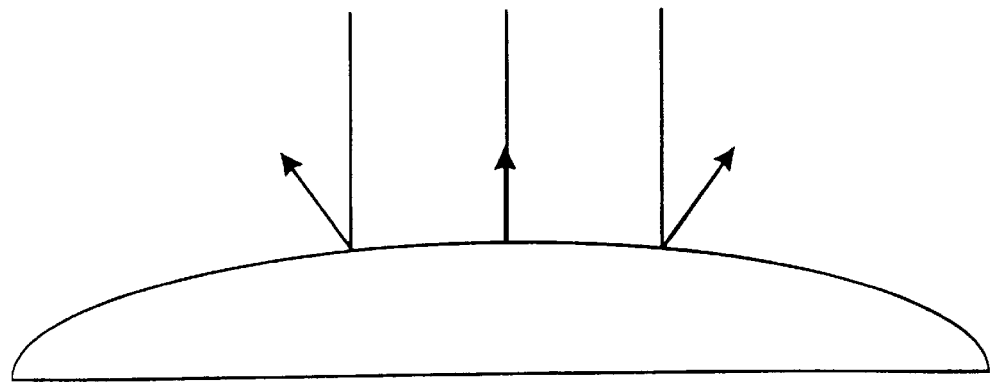
FIG. 5A illustrates a slightly convex mirror utilized to reflect the light of a light source.
Figure 5B:
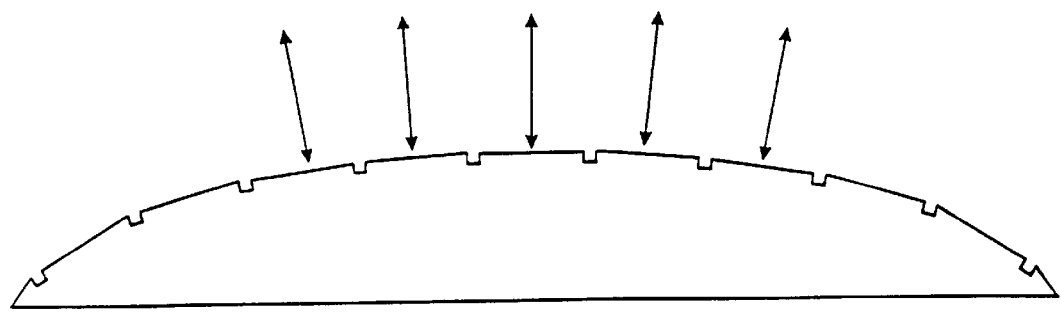
FIG. 5B illustrates a mirror having a plurality of flat facets on a convex spheroidal surface.

The mirrors of FIGS. 5A and 5B are preferred ways of implementing mirror 410 of FIG. 4.

FIG. 5A illustrates a slightly convex mirror utilized to reflect the light of a light source. Rays arriving displaced from a surface normally running through the center of curvature of the spheroidal mirror will be deflected slightly outside the beam width resulting in a slight beam spreading as illustrated.

FIG. 5B illustrates a mirror having a plurality of flat facets on a spheroidal surface. Flat facets, each highly reflective, form a plurality of small mirrored surfaces, each having a slightly different angular orientation with respect to a line joining the center of curvature of the spheroidal surface with the center of the mirror. When illuminated relatively uniformly with parallel rays, reflections from each facet on the spheroidal surface will have a slightly different angular orientation. One of the facets will best illuminate the aperture of the detector. By utilizing the mirror illustrated in FIG. 5B, alignment of the mirror with the laser source and the detector is somewhat less stringent than if only a single flat mirror were utilized.

Figure 6:
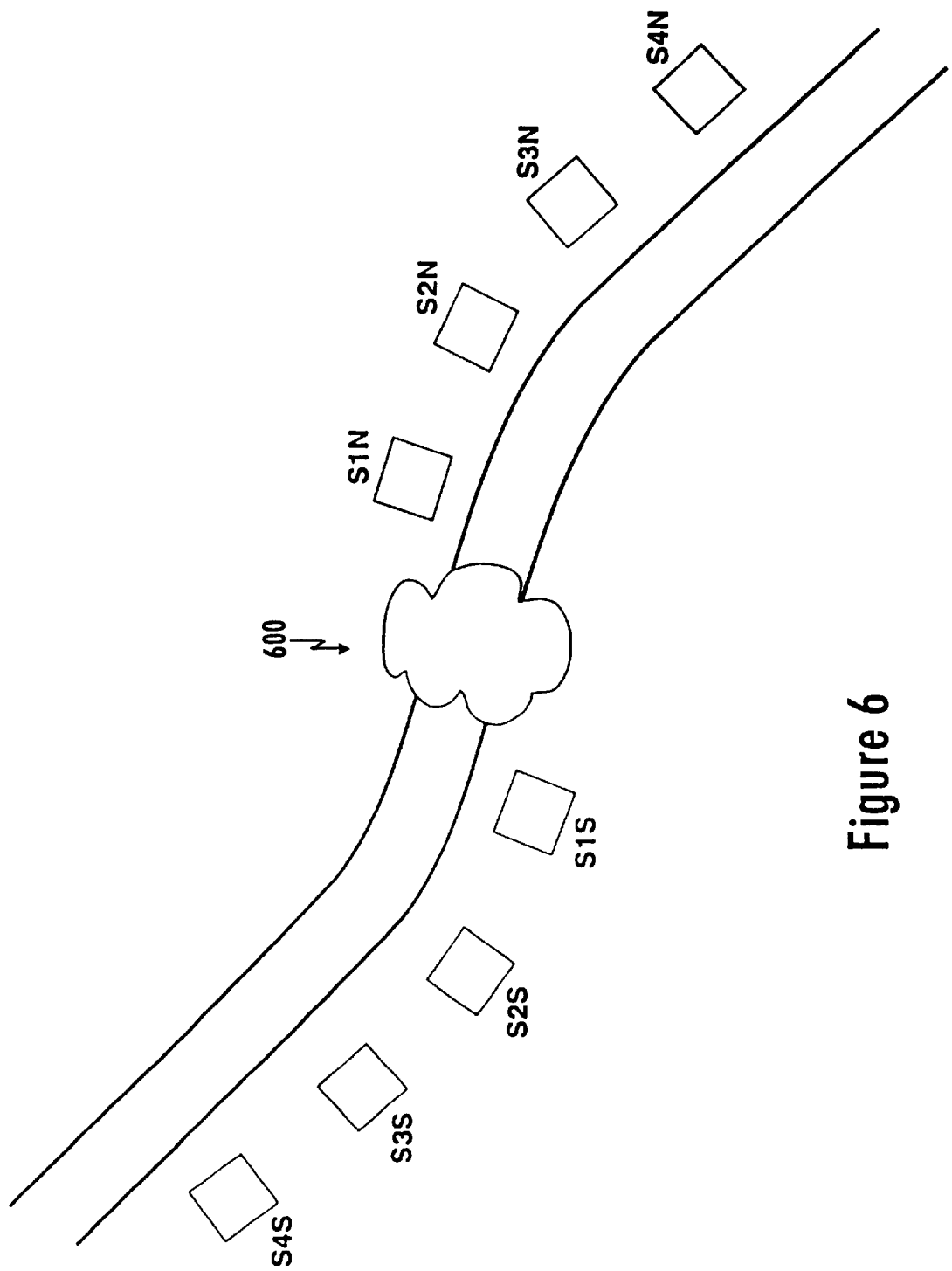
FIG. 6 illustrates a plurality of warning signs approaching a fog bank.

FIG. 6 illustrates a plurality of warning signs situated on different sides of the road approaching a localized fog bank on a highway. In the example illustrated in FIG. 6, signs S1N–S4N are situated on the north side of the highway and signs S1S–S4S are situated on the south side of the highway. Fog bank 600 has been determined through transmissometer readings to produce a visibility which permits a safe speed in the fog bank of 25 miles per hour. Cars approaching from the west on the south side of the highway need to slow down in an orderly fashion so that, when they enter the fog bank, they are at a speed which is reasonable for the visibility condition situated within the fog bank. A gradual slowing from whatever speed is being travelled under conditions of unrestricted visibility to a speed appropriate for the fog bank should be undertaken. This is accomplished, for example, by setting sign S4S to a speed of 55 miles per hour, S3S to a speed of 45 miles per hour, S2S to a speed of 35 miles per hour and sign S1 to a message which indicates the driver should maintain a 25 mile per hour speed within the fog bank. A similar gradual slowing should be imposed upon drivers arriving from the east on the north side of the highway. Thus, signs S1N–S4N contain messages corresponding to those of signs S1S–S4S, respectively.

It is possible to use warning systems other than warning signs. Information could be broadcast to vehicles at different lo,cations along the roadway using low powered AM or FM radio transmitters. In yet another alternative, each vehicle could carry an identification indicium such as an automatically readable smart card which transponds the vehicle's identity as it passes a sensing station. Knowing each vehicle's individual address, addressable transmission techniques such as random access discrete address or other techniques can be utilized to communicate with specific drivers. These specific communications could include messages tailored to a particular driver such as: "You are being rapidly overtaken by a vehicle from the rear. Please speed up."

In yet another embodiment, the warning system includes an automated override of the driver's desired speed to ensure that it does not exceed that which is safe for the conditions.

Figure 7A:
FIG. 7A–7D illustrate warning messages.
Figure 7B:
Figure 7C:
Figure 7D:

FIGS. 7A–7D illustrate warning messages illustrating the examples shown in conjunction with FIG. 6. FIG. 7A illustrates a message which would be appropriate for signs S4S and S4N in the example of FIG. 6. FIG. 7B illustrates a message which would be appropriate for signs S3S and S3N in FIG. 6. FIG. 7C illustrates a message which would be appropriate for signs S2S and S2N in FIG. 6. Finally, FIG. 7D illustrates a sign which would be appropriate for signs S1S and S1N.

Once within the fog bank illustrated in FIG. 6, conditions may change in such a way as to require adaptation of the message at signs S1S and S1N. For example, a radar detector might sense that traffic has slowed to an average of 10 miles per hour. In this case, even though the visibility in the fog bank would support a speed of 25 miles per hour, when the traffic is in fact going slower, allowing vehicles to enter the fog bank at 25 miles per hour when the traffic is only going 10, would surely result in accidents. Accordingly, the information content of the signs should be adapted in accordance with actual conditions of traffic within the fog bank as well as based on predicted or measured visibilities. The message displayed on signs S1S and S1N could therefore change to "Slow to 10 miles per hour" or "Brake now—stopped vehicles ahead."

Figure 8A:
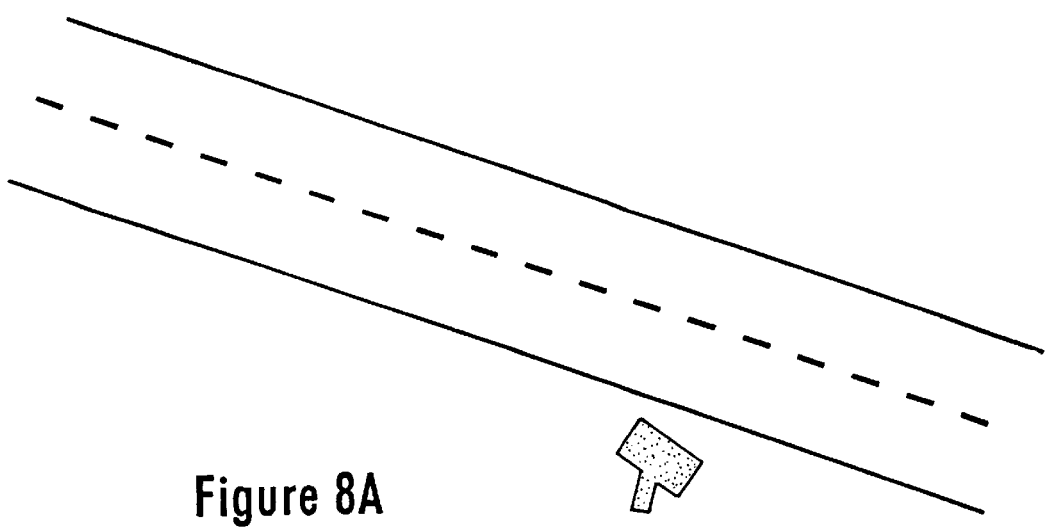
FIG. 8A illustrates a radar traffic sensor.

FIG. 8A illustrates a radar type of traffic sensor.

Figure 8B:
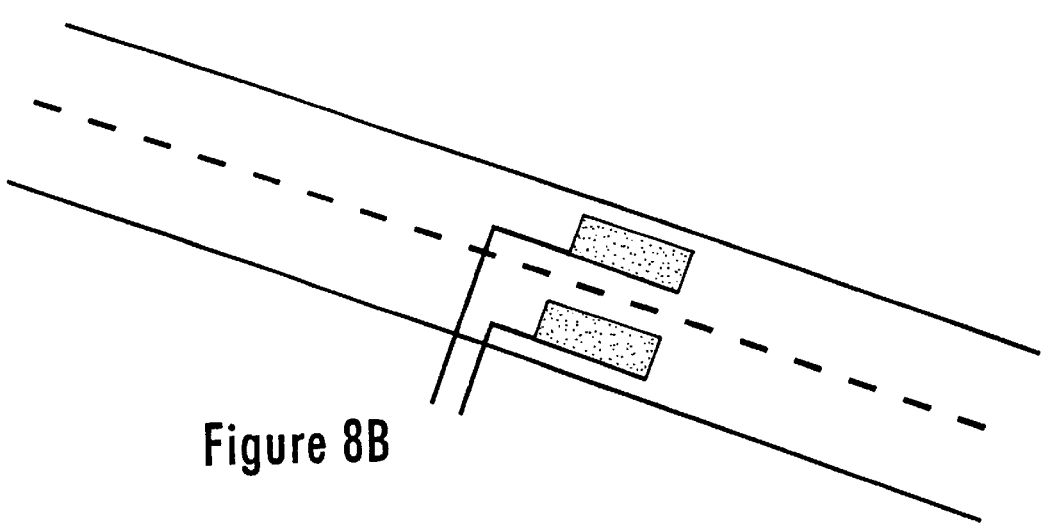
FIG. 8B illustrates a wire loop traffic sensor.

FIG. 8B illustrates a wire loop type of traffic sensor.

Figure 8C:
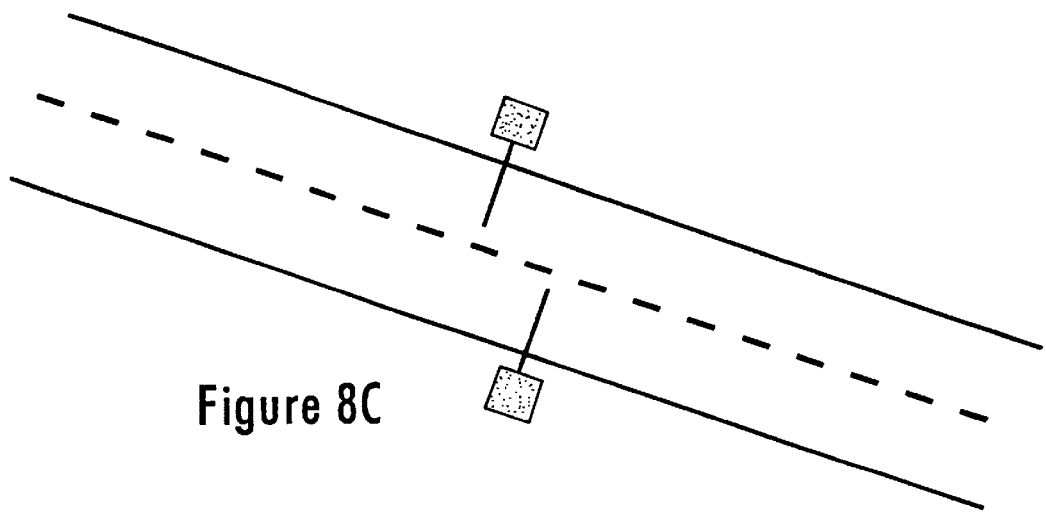
FIG. 8C illustrates a pneumatic traffic sensor.

FIG. 8C illustrates a pneumatic type of traffic sensor.

Although the traffic radar of FIG. 8A is a preferred method of detecting traffic conditions within a fog bank because it can distinguish slow or stopped traffic which accompanies an accident from no traffic, the wire loop detectors of FIGS. 8B or the pneumatic detector of FIG. 8C may have cost or other advantages.

Figure 9:
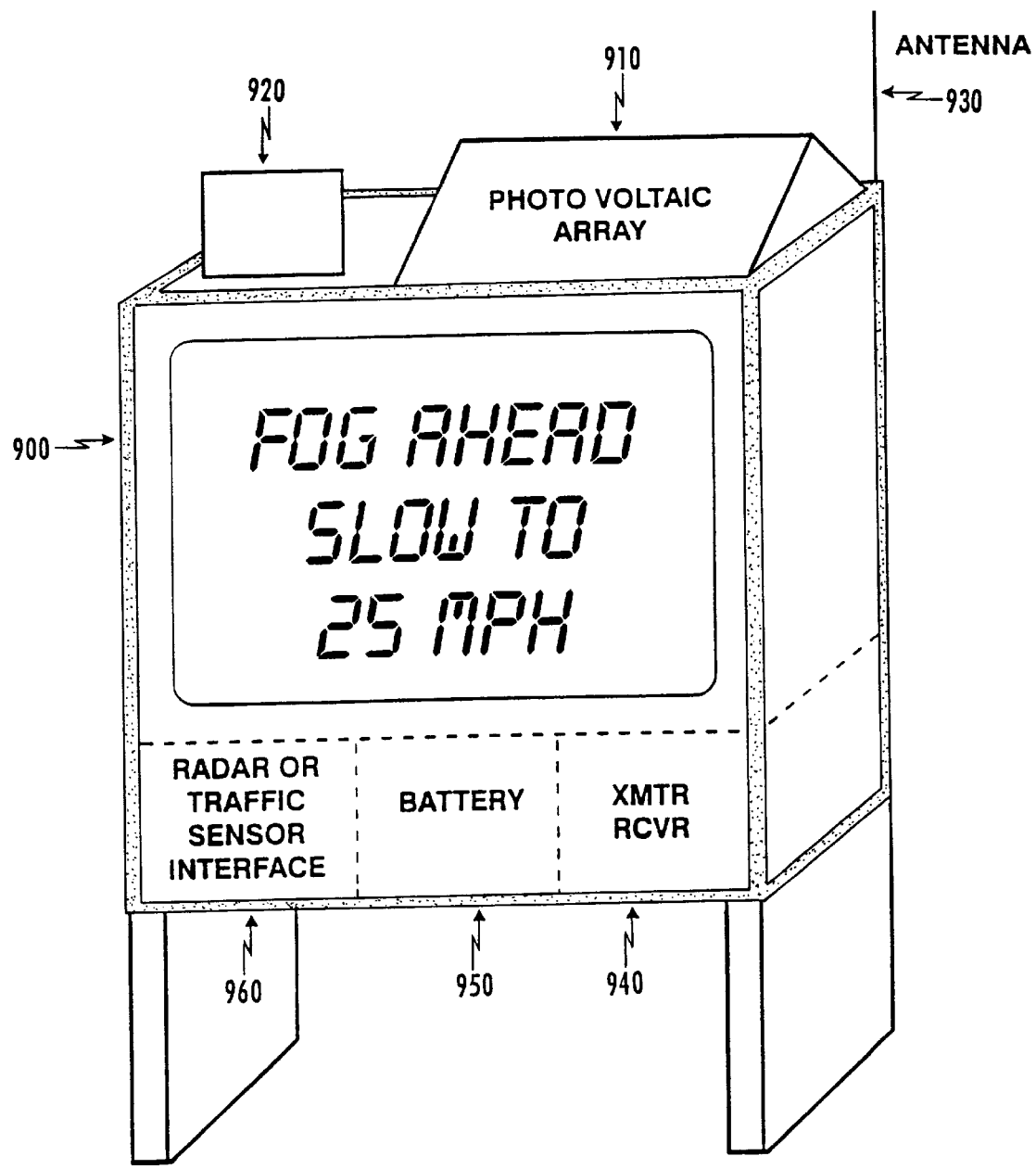
FIG. 9 illustrates a self contained integrated roadside unit for sensing traffic, communicating warning information to vehicles and transmitting information to and receiving information from a computer.

FIG. 9 illustrates a self contained integrated roadside unit for sensing traffic conditions, communicating warning information to vehicles and transmitting information to and receiving information from a computer. In the embodiment illustrated in FIG. 9, a warning sign 900 provides information to drivers. This sign unit is self-contained in that it is powered by a photovoltaic array 910 which converts solar energy to electric energy during periods of daylight and stores that energy in battery 950 for use during dark periods. The embodiment shown in FIG. 9 includes a mirror 920 which can be oriented to reflect a transmissometer light beam for measuring and detecting the presence of fog in the area of the unit shown in FIG. 9. The unit shown in FIG. 9 may include radar or a connection to traffic sensors of various sorts such as shown at 960. A transmitter/receiver 940 is linked to antenna 930 for communicating data about traffic conditions and environmental conditions to the central computer and for receiving control information from the computer specifying what messages to display to drivers. The unit is designed to be long lasting and can be either mounted permanently or movably adjacent a road.

Figure 10:
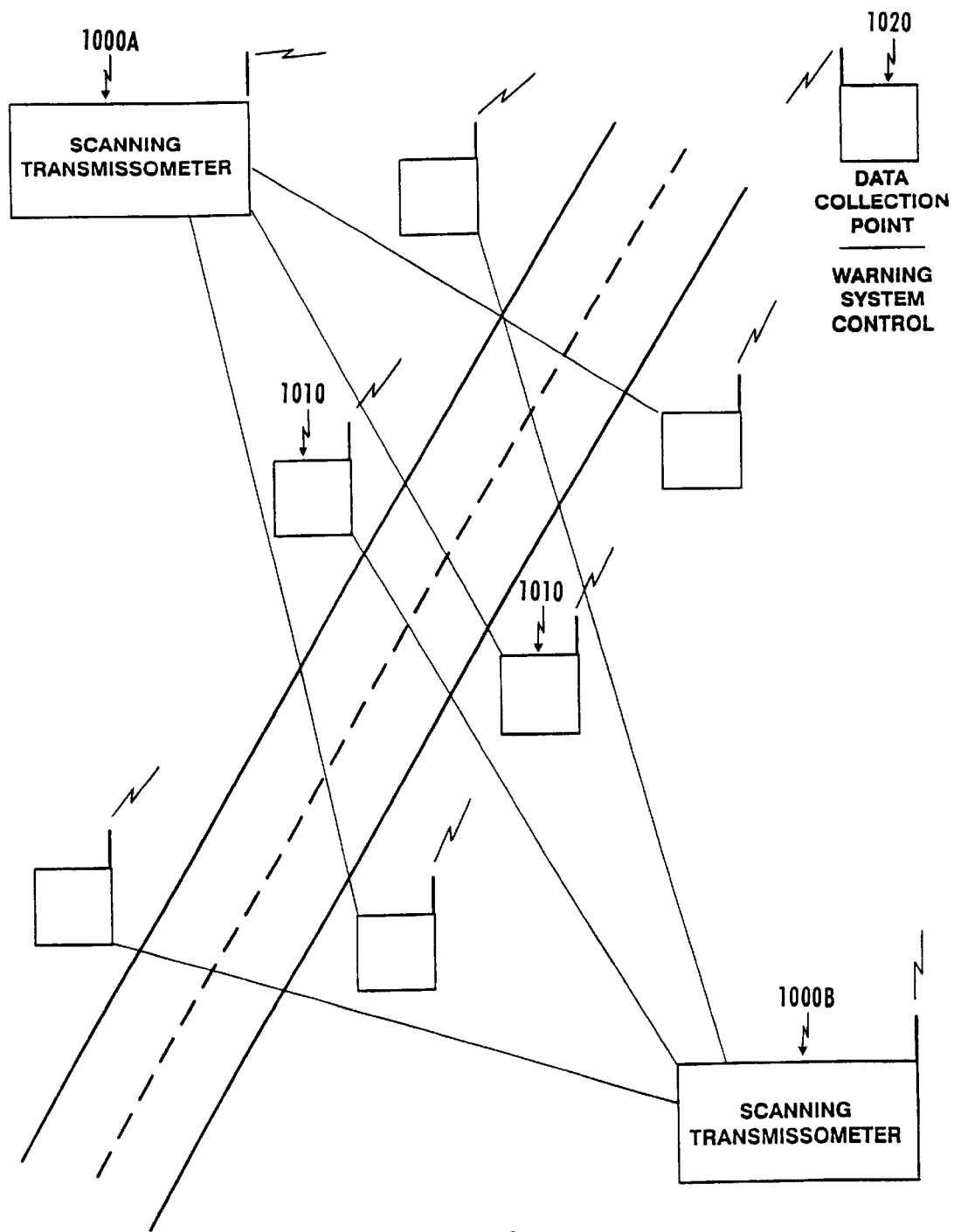
FIG. 10 illustrates scanning transmissometers arranged in a redundant configuration.

FIG. 10 illustrates scanning transmissometers arranged in a redundant configuration in accordance with the invention. Scanning transmissometers are shown more in detail in copending application Ser. No. 08/608,454, filed Feb. 28, 1996 entitled Computer Controlled Laser Fog Tracking, Bruce Tognazzini, the inventor of this application, filed concurrently herewith, which is hereby incorporated by reference in its entirety.

As shown in the embodiment in FIG. 10, scanning transmissometers 1000A and 1000B are situated on opposite sides of a highway. Each scanning transmissometer is paired with a set of reflectors (1010), if a transmissometer configuration shown in FIG. 4 is utilized, or with a set of detector locations, if the transmissometer configuration of FIG. 3 is utilized.

Preferably, the reflectors or detectors (1010) are mounted with or near low powered radio transmitters, each having a unique address (e.g. random access discrete address) and preferably powered by a lithium battery, which can be activated manually from the roadside to summon assistance. When activated, the address of the transmitter is transmitted to a receiver at the scanning transmissometer where the location of the transmitter is determined, based on its address, and where a request for assistance is generated and sent to a central data collection point (1010).

The FIG. 3 configuration is assumed for the FIG. 10 example. Periodically, the scanning transmissometers will scan each of the paired detectors located on the opposite side of the highway, which will make a determination, or the detector stations will make a determination, of the amount of signal received from the scanning transmissometers. If the signal is high in value, relatively, then little light has been scattered is and there is not much loss of visibility. If however, signal level received from the scanning transmissometers is very low, one may infer the presence of an environmental condition, such as fog, which will reduce visibility.

Each detector 1010 is linked via a communication link with a central data collection point 1020 at which the computer controlling the traffic warning system is situated. Communications may occur, as illustrated, over a radio link using any number of communications protocols that might be suitable. If radio is utilized as the communications link, a carrier sense multiple access/collision detection (CSMA/CD) system, such as Aloha or slotted Aloha is preferred. If all stations are linked by a communications bus, one might prefer to utilize poll select or a different protocol.

The embodiment shown in FIG. 10 has the advantage of redundance. For example, if a scanning transmissometer (e.g. 1010A) on one side of the road were itself to become obscured in fog, reflector/detector stations on the opposite side of the road would not receive a very strong signal and would all report fog. If, however, the scanning transmissometer on the opposite side of the road did not suffer from that defect, then its readings would indicate clearer or at least the appropriate value of visibility detected by the instrumentation. Thus, the redundant configuration permits good information to be obtained even in the presence of a partial system failure.

In the embodiments shown in FIGS. 6 and 10 reflectors can be utilized with scanning transmissometers and the reflectors can be simple mirrors located on telephone poles at periodic intervals.

Figure 11:
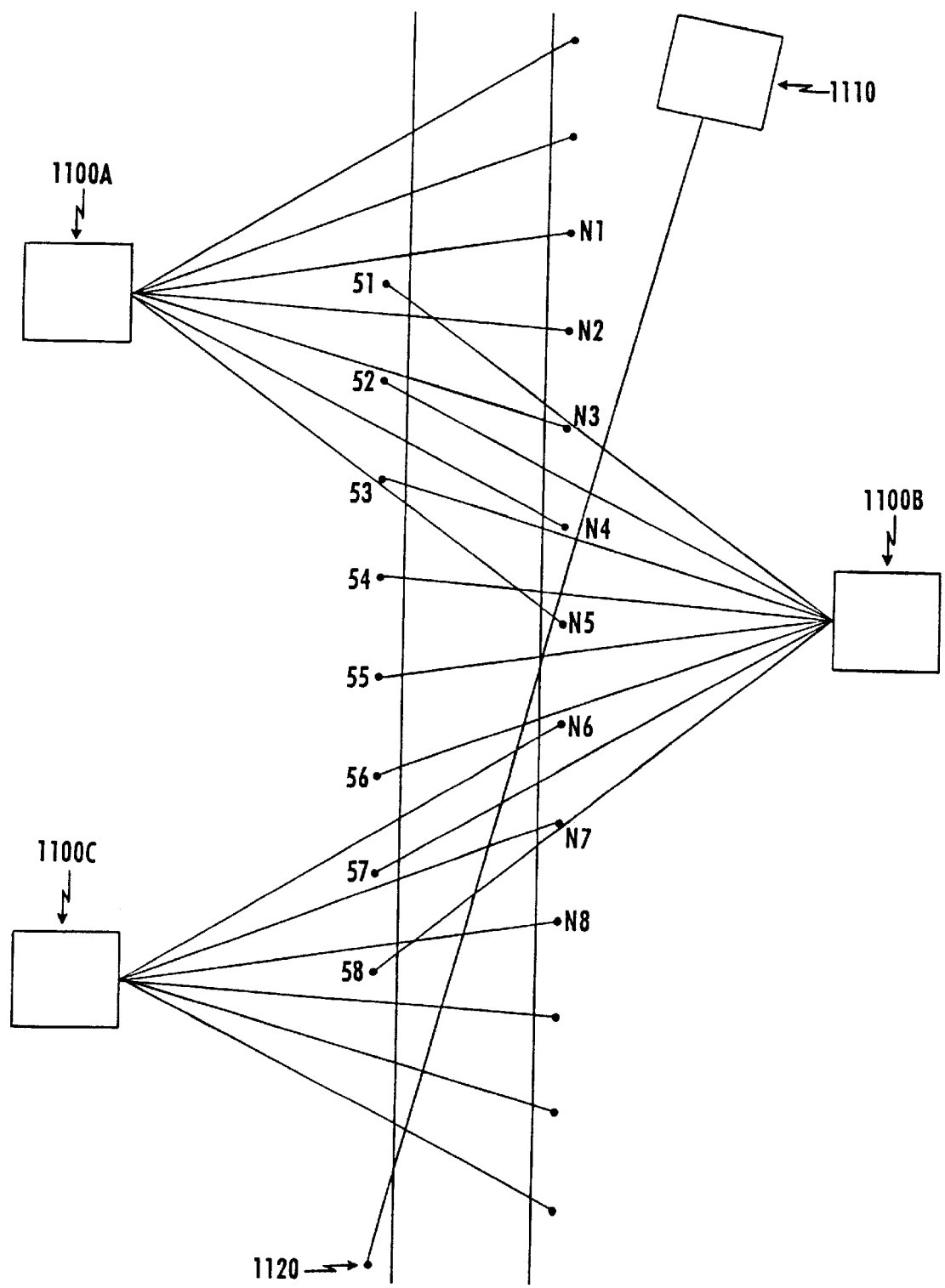
FIG. 11 illustrates an arrangement of scanning transmissometers arranged in a redundant overlapping interlaced configuration with a fixed transmissometer used to validate information from the scanning transmissometers.

FIG. 11 illustrates an arrangement of scanning transmissometers arranged in a redundant overlapping interlaced configuration with a fixed transmissometer utilized to validate information from the scanning transmissometers. In the embodiment shown in FIG. 11, scanning transmissometers 1100A, 1100B and 1100C are arranged in a redundant, overlapping interlaced configuration. Each scanning transmissometer scans its set of reflector/detector stations, e.g. S1–S8 in FIG. 11, and reports the detected transmissometer reading to the central computer. The use of scanning transmissometers and simple passive reflectors results in a very cost effective implementation. Instead of large numbers of transmissometers, only large numbers of much cheaper reflectors are required for relatively few scanning transmissometers. Because of the economical nature of the implementations disclosed herein, additional levels of redundance may be cost effective. Such an additional level of redundance is illustrated in FIG. 11 in which a fixed transmissometer 1110 is designed to provide a sensing path which extends over a much greater length than the normal transmissometer detector pair paths and over a path which is much more nearly parallel to the path of an extended stretch of road than that utilized by the scanning transmissometers. Thus, if the road is reasonably straight for 8 or 10 miles, a fixed transmissometer could be aligned to almost parallel the road, finally crossing the road at a reflector or detector point many miles away. Such a configuration is useful for detecting certain types of system failures which might otherwise not be detected. For example, if fog were encroaching on one side of the road only, in such a way that both scanning reflectometers 1100A and 1000C were obscured, and some of the detectors S1–S8 of scanning reflectometer 1000B were obscured, the road might nevertheless be clear. Under these circumstances, fixed transmissometer 1110 would illuminate detector 1120 indicating a clear road, notwithstanding a very strong indication from the scanning reflectometers that the road is obscured with fog.

FIG. 12 illustrates sample stopping distance data utilized to infer safe speed. The values shown in the table in FIG. 12 are not intended to be accurate representations of stopping distance but rather to be exemplary of the kinds of traffic engineering data available to traffic engineers which would be useful in determining safe speed. For example, reaction distance assumes a fixed reaction time of ½ second. In actuality, reaction times are faster than this. Similarly, stopping distance is calculated using certain assumptions about constant deceleration which may or may not reflect the judgment, experience and factual data available to a traffic engineer. What is important is that traffic engineering data can be organized in the manner shown in FIG. 12, and that safe speed can be determined by determining the visibility in feet at a given location and then either interpolating or using the next lower speed from a table such as that shown above, to infer a proper safe speed for the amount of visibility available. Preferably, accidents are best avoided when the safe speed is such as to permit stopping within the distance visible under foggy conditions.

FIGS. 13A–13C illustrate how to calculate a safe speed in a way which minimizes convoy effect. FIG. 13A illustrates the safe speeds associated with detection points on the north side of a highway, namely points N1–N8. FIG. 13B illustrates safe speeds associated with detection points on the southern portion of the same highway, namely at points S1–S8. In FIG. 13C, the points from FIGS. 13A and 13B are plotted as a function of distance along the highway.

Considering, points N4 and S4 and points N7 and S7, the relatively low safe speed ratings for these points indicates a foggy condition. It is clear that at these four points, one should desire to reduce the speed of incoming vehicles to a point where they will not be endangered by the sudden loss of visibility. In the case of points N4 and S4, one desires to reach a speed of 10 miles per hour. Preferably this is achieved gradually so that accidents don't occur and so that drivers can make the change in a controlled and gradual manner. One would prefer that the speed decrease, in the case of FIG. 13C, linearly from whatever was permitted before the fog bank to a speed appropriate for the fog bank. This decrease in speed is illustrated at line 1310. At line 1320, one should notice that although a safe speed for traffic engineering purposes might be 80 miles per hour, the speed limit for the area in question is only 70 miles per hour. Thus, the safe speed is limited at line 1320 to that permitted by the state. As desired, the speed between points N4 and S4 is at 10 miles per hour (1330). Since at point N5, the historical safe speed indicates 50 miles per hour, it is not desirable to allow the speed to increase to 50 miles per hour immediately upon exiting the fog bank. Doing so would exacerbate convoy effect and likely lead to accidents because at point S5, the safe speed drops back down to 30 miles per hour.

At points N7 and S7, the safe speed is only 5 miles per hour. Similarly, one would desire to achieve a gradual reduction in speed from whatever was permitted before to the 5 mile per hour level. This is reflected at line 1350. Once in the fog bank, the speed should be that shown at line 1360, and, upon emerging from the fog bank, the speed may increase in a measured manner from 5 miles per hour to whatever is safe at point S8, namely, 40 miles per hour.

Thus, one can see from FIG. 13C that although at specific points along the highway, safe speed might actually be above that imposed by the system, by choosing the lower of the safe speed or the profile speed needed to achieve a proper speed in a fog bank, one minimizes the convoy effect and permits traffic to flow in an orderly manner.

Figure 14:
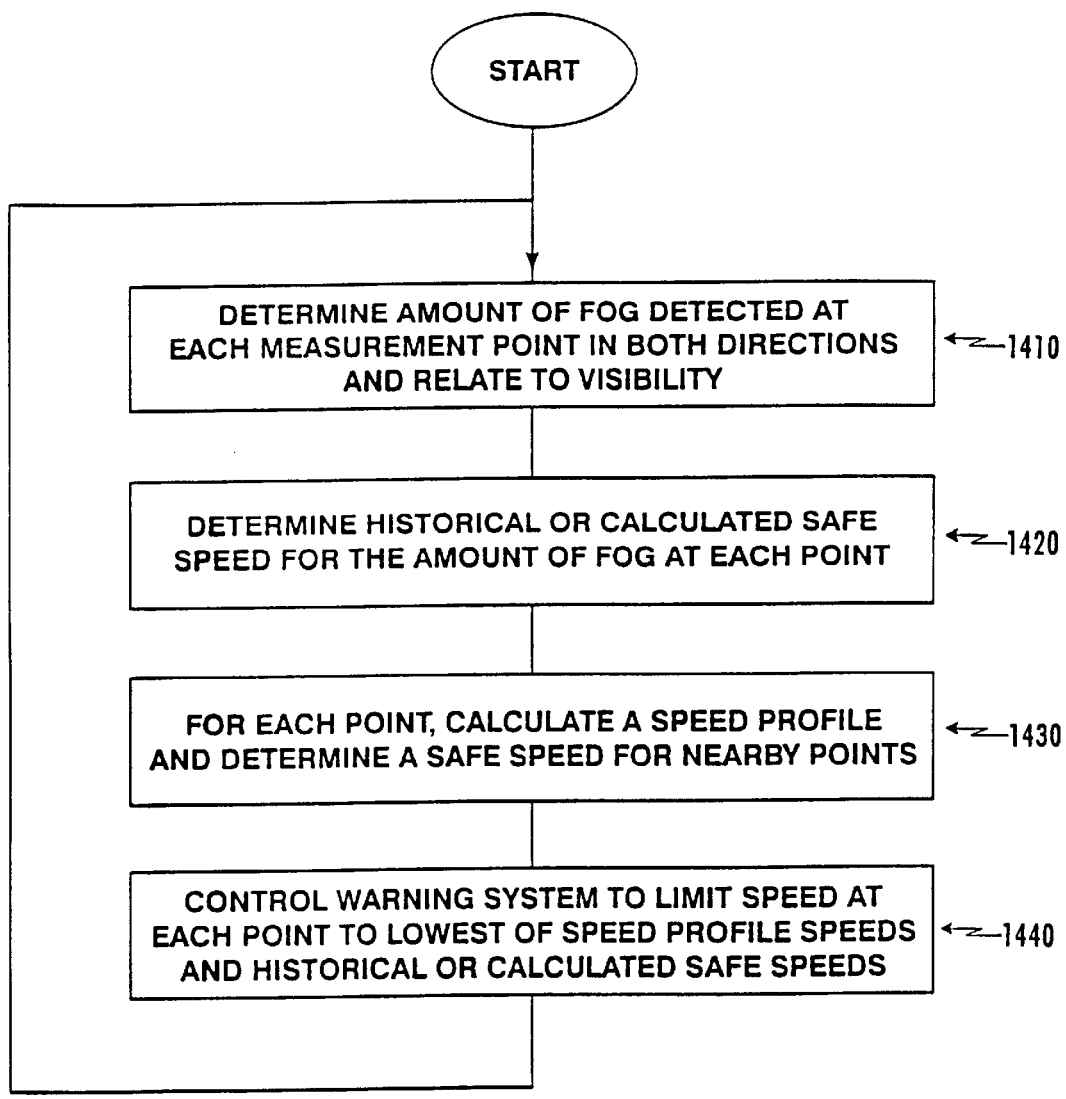
FIG. 14 illustrates a flow chart of a process for determining safe speed.

FIG. 14 is a flow chart of a process for determining safe speed. The process of FIG. 14 begins by determining the amount of fog detected at each measurement point in both directions and relates that amount to fog visibility (1410). Tables are utilized to determine an historical or calculated safe speed for the amount of fog at each point (1420). For each point along the highway, a speed profile is calculated and a determination made of a safe speed for nearby points (1430). At 1440, the warning system is controlled to limit the speed at each point to the lower of (1) the lowest of the speed profile speeds or (2) the historically calculated safe speed.

FIG. 15 illustrates a look up table linking transmissivity with visibility for particular measurement points. The amount of visibility associated with transmissivity measured by the transmissometers, potentially varies from measurement point to measurement point. It may also vary with factors not illustrated in FIG. 15 such as time of day. One may also expect some statistical variations in the relationship between visibility and transmissivity. Look up Table 15 is best created by calibration measurements at each measurement point during installation of the roadway. The particular value or values selected for visibility at a given level of measured transmissivity should preferably reflect a judgment which conservatively will result in safe speeds regardless of statistical or systemic variations in parameters.

Figure 16:
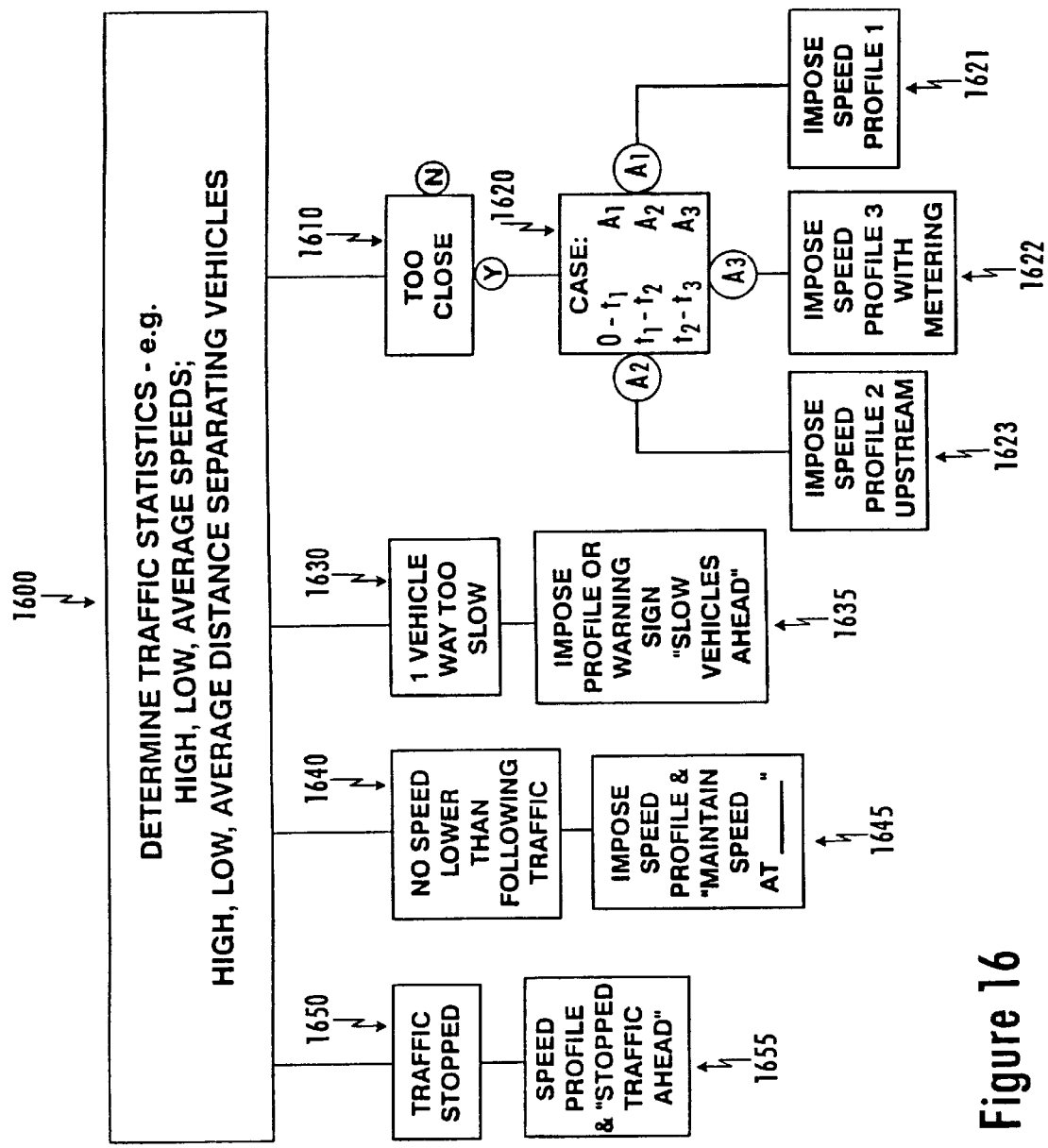
FIG. 16 illustrates a flow chart for additionally modifying warning information based on traffic sensor information.

FIG. 16 illustrates a flow chart for additionally modifying warning information based on traffic sensor information. Even though the set of safe speeds established in accordance with this invention should result in relatively safe conditions when experiencing fog on a roadway, some drivers behave in ways which ignore the warning system. Under those circumstances, it is desired that the safe speeds be modified to reflect actual traffic conditions on the roadway rather than merely assuming compliance on the part of the drivers. FIG. 16 illustrates a way in which this may be done. The integration of the traffic control information from the traffic sensors allows the control system to reflect the realities of traffic conditions on the road. As shown in FIG. 16, at block 1600, it is desired to utilize the traffic information received from the traffic detectors to determine certain traffic statistics, typically, high, low and average speeds and high, low and average distance separating vehicles. If the average distance separating vehicles indicates that the vehicles are too close (1610), the action to be taken depends upon the amount of closeness (1620). One action might be taken if the closeness lies between 0 and threshold T1. Another may be taken if the closeness exceeds T1 but is less than or equal to T2 and yet a third action may be taken if the threshold exceeds T2 but is less than or equal to T3. In the first case, one may wish to impose a particular speed profile 1 (1621). In the second condition, one may impose a different speed profile 2 (1623) extending further upstream of where the traffic statistics are sampled. Finally, if the third threshold is exceeded, one might impose a more austere speed profile 3 (1622) and impose traffic metering.

A determination of the lowest speed for a vehicle on the road permits one to determine if one vehicle is moving much, much slower than the other vehicles (1630). This permits one to impose an appropriate speed profile upstream of the location of the slow vehicle or to assert a warning to the drivers of vehicles that there are, e.g., "slow vehicle ahead" (1635).

If the traffic statistics indicate that the average speed is lower than that of the following traffic (1640), one could impose a speed profile upstream (1645) before the measurements are taken and impose a warning to "maintain speed" at a particular value for vehicles downstream of the point where the measurements are taken.

If the traffic statistics indicate that the traffic has stopped (1650), one could impose the speed profile upstream of the location where the traffic is stopped with the notation "traffic stopped ahead" or, if the traffic was stopped very close to the location of the warning sign, one might assert a message "begin breaking now."

By using the apparatus and methods disclosed herein, the problem for adequately detecting and notifying drivers of traffic conditions resulting from very small but dense pockets of fog are encountered suddenly and without warning by vehicles travelling in an otherwise clear area. The invention provides credible warnings automatically and adapts to the actual behavior of vehicles encountering fog on the road. The invention permits drivers to avoid the convoy effect if they adhere to warnings provided by the system.

In this disclosure, there is shown and described only the preferred embodiment of the invention, but, as aforementioned, it is to be understood that the invention is capable of use in various other combinations and environments and is capable of changes or modifications within the scope of the inventive concept as expressed herein.

I claim:

1. A traffic control system comprising:
   a. one or more environmental condition detectors; wherein each detector determines visibility at a plurality of points along a road;
   b. one or more traffic sensors;
   c. one or more warning devices; and
   d. a computer, receiving first information from said one or more environmental condition detectors and second information from said one or more traffic sensors, configure to control said one or warning devices to provide drivers with information useful to avoid accidents base on said first and second information.

2. The traffic control system of claim 1 in which said one or more environmental condition detectors is a fog detector.

3. The traffic control system of claim 2 in which said fog detector is a scanning transmissometer.

4. The traffic control system of claim 3 in which a reflector or detector of the transmissometer is mounted with or near a low powered radio transmitter.

5. The traffic control system of claim 1 in which said one or more traffic sensors detects traffic speed and separation.

6. The traffic control system of claim 1 in which said one or more warning devices is a warning sign.

7. The traffic control system of claim 1 in which said one or more warning devices is a radio broadcast device.

8. The traffic control system of claim 1 in which said computer is configured to select information for a warning device based on a speed profile.

9. The traffic control system of claim wherein said transmissometer comprises a light source for passing light through a region on a road and a detector for detecting light passing through said region on said road.

10. The traffic control system of claim 9 wherein said transmissometer further comprises a chopper for modulating said light source which facilitates detection by said detector.

11. The traffic control system of claim 9 wherein said transmissometer further comprises a reflector that reflects said light emanating from said light source to said detector.

12. The traffic control system of claim 11 wherein said reflector is a convex mirror.

13. The traffic control system of claim 12 wherein said reflector comprises flat facets arranged at slightly different angles to form a convex-type surface.

14. The traffic control system of claim 12 wherein the number of reflectors is greater than the number of detectors in each transmissometer.

15. The traffic control system of claim 1 wherein said warning device comprises a smart card detector for detecting a smart card associated with a passing car, said smart card having an identification code used to identify the passing car, said identification code used by said warning device to directly communicate with said passing car.

16. The traffic control system of claim 1 wherein said traffic sensor comprises at least one of a radar sensor, a wire loop sensor, and a pneumatic sensor.

17. The traffic control system of claim 1 wherein said traffic sensor, said warning device and said computer are located with a housing unit, having a unique address, wherein said housing unit is powered by a photovoltaic array.

18. The traffic control system of claim 17 wherein said housing unit further comprises a signaller and a manually activated switch used to activate said signaller for summoning assistance to said housing unit based on said unique address.

19. The traffic control system of claim 1 wherein said traffic control system comprises a plurality of environmental condition detectors located on opposite sides of a road and arranged in a redundant, overlapping interlaced configuration to provide redundant detecting of a regions on said road.

20. A method for traffic control, comprising the steps of:
 a. providing at least one element for performing the step of detecting environmental conditions to determine visibility at a plurality of points along a road;
 b. providing at least one element for performing the step of sensing traffic conditions;
 c. providing at least one element for performing the step of providing drivers with information based on a speed profile derived from at least one of environmental conditions and traffic conditions.

21. A computer implemented process for providing information to drivers approaching a warning device positioned along a road, comprising:
 a. providing at least one element for performing the step of detecting environmental conditions to determine visibility in an area near the warning device and at points further along the road in the direction of travel;
 b. providing at least one element for performing the step of detecting speed or separation of traffic in said area; and
 c. providing at least one element for performing the step of controlling the warning device to communicate a safe speed to said drivers based on a speed profile derived from environmental conditions at one or more points along the road and on traffic speed or separation.

22. A computer readable medium containing a process in computer program form for controlling one or more warning devices based on inputs received from environmental condition detectors and from traffic sensors, the process comprising:
 a. detecting environmental conditions to determine visibility in an area near the warning device and at other points and
 b. controlling the warning device to communicate a safe speed to said drivers based on a speed profile derived from environmental conditions in said area and at said other points.

23. The computer readable medium of claim 22 in which said process further comprises detecting speed and/or separation of traffic in said area and modifying said speed profile based on traffic speed or separation.

24. A safety enhanced road comprising:
 a. a section of road with one or more environmental condition detectors positioned along said section of road to determine visibility at a plurality of points along said section of road and with one or more traffic sensors positioned along said section of road;
 b. one or more warning devices configured to provide information to drivers on said road;
 c. a computer for determining said information based on at least one of input from said one or more environmental condition detectors and said one or more traffic sensors.

25. A safety enhanced road comprising:
 a. a plurality of scanning transmissometers positioned along a road, each detecting visibility at a plurality of locations and transmitting results of detection to a central traffic control computer;
 b. one or more traffic sensors positioned along said section of road each transmitting results of sensing to said central traffic control computer;
 c. one or more warning devices configured to provide safety information to drivers on said road, said safety information being transmitted to said warning device from said central traffic control computer; and
 d. said traffic control computer configured to determine said safety information based on at least one of said results of detection and said results of sensing.

26. The safety enhanced road of claim 14, further comprising a fixed transmissometer measuring visibility along the length of said road.

27. A method for traffic control, comprising:
 a. providing at least one element for performing the step of determining visibility at a plurality of points along a road;
 b. providing at least one element for performing the step of selecting a predetermined safe speed for each point based on the visibility at that point;
 c. providing at least one element for performing the step of determining a speed profile specifying a safe speed for nearby points based on conditions at a point; and
 d. providing at least one element for performing the step of controlling a warning system to impose a speed limit on a segment of road to the lowest of the speed profile speeds required by nearby points and said predetermined safe speed.

28. The method of claim 27 further comprising providing at least one element for performing the step of modifying the value of said speed limit based on traffic conditions.

29. The method of claim 27 further comprising requiring a minimum speed be maintained in conditions of reduced visibility and modifying said minimum speed based on actual traffic conditions.

30. A computer readable medium containing a process for controlling traffic based on visibility at points along a road in computer program form for:
 a. determining visibility at a plurality of points along a road;
 b. establishing a predetermined safe speed for each point based on the visibility at that point;
 c. determining a speed profile specifying a safe speed for nearby points based on conditions at a point; and
 d. controlling a warning system to impose a speed limit on a segment of road to the lower of (1) the lowest of the speed profile speeds required by nearby points and (2) said predetermined safe speed.

* * * * *

UNITED STATES PATENT AND TRADEMARK OFFICE
CERTIFICATE OF CORRECTION

PATENT NO. : 5,771,484
DATED : June 23, 1998
INVENTOR(S) : Bruce Tognazzini

It is certified that error appears in the above-indentified patent and that said Letters Patent is hereby corrected as shown below:

In the claims:

Claim 1, line 10, change "configure" to --configured--;
after "or", insert --more--;
Claim 9, line 1, after "claim" insert "1";
Claim 22, line 8, after "points" insert ";";
Claim 23, line 2, change "and/or" to --or--;
Claim 26, line 1, change "14" to --25--.

Signed and Sealed this

Sixteenth Day of February, 1999

Attest:

Attesting Officer

*Acting Commissioner of Patents and Trademarks*